(12) United States Patent
McMillian (10) Patent No.: US 11,773,457 B2
(45) Date of Patent: Oct. 3, 2023

(54) **ASSAY FOR *TRICHOMONAS VAGINALIS* BY AMPLIFICATION AND DETECTION OF *TRICHOMONAS VAGINALIS* AP65-1 GENE**

(71) Applicant: BECTON DICKINSON AND COMPANY, Franklin Lakes, NJ (US)

(72) Inventor: Ray A. McMillian, Timonium, MD (US)

(73) Assignee: BECTON, DICKINSON AND COMPANY, Franklin Lakes, NJ (US)

(*) Notice: Subject to any disclaimer, the term of this patent is extended or adjusted under 35 U.S.C. 154(b) by 0 days.

(21) Appl. No.: 17/408,374

(22) Filed: Aug. 21, 2021

(65) Prior Publication Data

US 2022/0090214 A1 Mar. 24, 2022

Related U.S. Application Data (60) Division of application No. 15/969,216, filed on May 2, 2018, now Pat. No. 11,124,844, which is a continuation of application No. 14/576,361, filed on Dec. 19, 2014, now Pat. No. 9,988,692, which is a division of application No. 12/686,695, filed on Jan. 13, 2010, now Pat. No. 8,945,842.

(60) Provisional application No. 61/205,017, filed on Jan. 14, 2009.

(51) Int. Cl.
*C12Q 1/6893* (2018.01)

(52) U.S. Cl.
CPC ..... *C12Q 1/6893* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| 5,922,563 | A | 7/1999 | Alderete |
| 8,323,897 | B2 | 12/2012 | Andersen et al. |

OTHER PUBLICATIONS

Examination Report dated Apr. 4, 2017 in European Application No. 16161924.2.
Final Office Action dated Jul. 18, 2012 in U.S. Appl. No. 12/686,695.
Final Office Action dated Mar. 14, 2014 in U.S. Appl. No. 12/686,695.
Final Office Action dated Apr. 26, 2017 in U.S. Appl. No. 14/576,361.
Final Office Action dated Jan. 3, 2018 in U.S. Appl. No. 14/576,361.
Final Office Action dated Aug. 4, 2020 in U.S. Appl. No. 15/969,216.
Non-Final Office Action dated Jan. 12, 2012 in U.S. Appl. No. 12/686,695.
Non-Final Office Action dated Nov. 4, 2016 in U.S. Appl. No. 14/576,361.
Non-Final Office Action dated Aug. 18, 2017 in U.S. Appl. No. 14/576,361.
Non-Final Office Action dated Apr. 8, 2020 in U.S. Appl. No. 15/969,216.
Notice of Allowance dated Sep. 16, 2014 in U.S. Appl. No. 12/686,695.
Notice of Allowance dated Mar. 24, 2016 in European Application No. 10701589.3.
Notice of Allowance dated Feb. 7, 2018 in U.S. Appl. No. 14/576,361.
Notice of Allowance dated May 25, 2021 in U.S. Appl. No. 15/969,216.
Extended European Search Report for Application No. EP16161924.2 dated Aug. 2, 2016.
International Search Report and Written Opinion, PCT/US2010/020989, dated Apr. 21, 2010.
Alderette, J. F., et al., "Cloning and molecular characterization of two genes encoding adhesion proteins involved in trichomonas vaginalis cytoadherence", Molecular Microbiology, Wiley-Blackwell Publishing Ltd, vol. 17, No. 1, Jan. 1, 1995, XP002969893., (Jan. 1, 1995), pp. 69-83.
Arroyo, R., et al., "Characterization of cDNAs encoding adhesin proteins involved in trichomonas vaginalis cytoadherence", Archives of Medical Research, Instituto Mexicano Del Seguro Social, Mexico, MX, vol. 26, No. 4, Jan. 1, 1995, XP002969891., (Jan. 1, 1995)., pp. 361-369.
Caliendo, et al., "Real-time PCR improves detection of Trichomonas vaginalis infection compared with culture using self-collected vaginal swabs", Infectious Diseases and Gynecology, Sep. 2005, vol. 13, No. 3, (Sep. 2005), pp. 145-150.
Madico, G., et al., "Diagnosis of Tri chomonas vaginalis infection by PCR using vaginal swab samples", Journal of Clinical Microbiology Nov. 1998 LNKD—PUBMED:9774566, vol. 36, No. 11, Nov. 1998, XP009131786, (Nov. 1998), pp. 3205-3210.
Mahmoud, M. S., et al., "Diagnosis of symptomatic and asymptomatic Trichomonas vaginalis infection by applying one tube nested PCR to vaginal discharge", "Journal of the Egyptian Society of Parasitology" vol. 29, No. 3, Jan. 1, 1999, XP009131567, (Jan. 1, 1999), pp. 1031-1046.
Riley, D. E., et al., "Development of a polymerase chain reaction-based diagnosis of Trichomonas vaginal is", Journal of Clinical Microbiology, American Society for Microbiology, Washington, DC, US, vol. 30, No. 2, Feb. 1, 1992, XP009131613, (Feb. 1, 1992), pp. 465-472.

*Primary Examiner* — Young J Kim
(74) *Attorney, Agent, or Firm* — Sheppard, Mullin, Richter & Hampton LLP (57) ABSTRACT

A region of the *Trichomonas vaginalis* AP65-1 gene has been identified which is useful for performing amplification assays to determine specifically whether *T. vaginalis* is present in the sample being tested. Oligonucleotides useful for performing thermal Strand Displacement Assay (tSDA) reactions on this gene are disclosed. The disclosed oligonucleotides can be used in an assay which is specific for multiple strains of *T. vaginalis* and which does not show cross reactivity with the genomes of other microorganisms or with human DNA.

20 Claims, 3 Drawing Sheets
Specification includes a Sequence Listing.

SEQUENCE LISTING

```
<160> NUMBER OF SEQ ID NOS: 24

<210> SEQ ID NO 1
<211> LENGTH: 1751
<212> TYPE: DNA
<213> ORGANISM: Trichomonas vaginalis

<400> SEQUENCE: 1 ttttgatta aagatgctta catcttcagt ctctcttcca gcacgtgaac tctcccgcaa      60
ggttctccca accctcaaga caggaatgac cttacttcag gatggagatc tcaacaaagg     120
tacagctttc acaaaagaag aacgtgaccg cttcaatctt cgtggcctcc tcccatacaa     180
ggtcttcaca aaggatgaac aagctgctcg tatccgccgc cagttcgagt tgatgccaac     240
accactcctc aagtacatct tcctcgccaa cgagcgtgag aagaactcac agtccttctg     300
gagattcctc ttcacacacc caccagagga aacaatgcca attctttaca caccaactgt     360
cggtgaagct tgccagaagt gggctacaca ccgtcaatca taccgcggca tctacatcac     420
accagaagat tctggcaaga tcaaggacat cctccgcaac tacccacgcc aggacatccg     480
ctgcattgtc gttacagatg ctggccgtat tctcggtctc ggcgatctcg gtgcttccgg     540
ccttggtatt ccagttggta agcttatgct ttacacactt atcggccaag ttgacccaga     600
tcagacactt ccagtccagt tagatatggg tacagacaga aaggaaatcc tcgccgaccc     660
actctaccac ggctggcgcc atccacgtgt acgtggcgct gagcacctca gttcgtcac      720 agaattcgtt gaggcagtca aggaagtctt cggtgacaca tgccttgtcc agttcgaaga    780
tttcgaaatg gaaactgctt tcaagcttct cgaccacttc agatggcgct gcaactgctt    840
caacgatgat atcgaaggta cagctgccgt tgctgctgct acacttgctt cagctacaca    900
catggaaggt gttccagatc tcaagaacca gaagatcatc ttcatcggtg ctggctctgc    960
tgccataggc attgctaacc tcattgtcga tatgacagtt tcccgcggtg gcatcaccaa   1020
```

-continued

```
ggagcaagcc ttcaagaaca tcatcatgtt cgatcaccgt ggcatggtcc atgctggccg      1080
taaggatctc tacgacttca acaagccata catgcacgac atggaagtct acggctcagt      1140
tctcgaggcc gtcaagaagt tcaaggctac atgcgtcatt ggtgtttccg gtgttccagg      1200
actcatcaca aaggaaatcg tccaggcaac attaaagaat gctgagcacc cagtcatcat      1260
gccactttcc aacccaacac caaaggctga agctacacca cacgatgttt acctttggtc      1320
caatggcaag gccctctgcg ctacaggctc accattccca gccgaacaag tcaacggcag      1380
aaaggtcatc actgcccaag ctaacaactc ctggatcttc ccagctgttg gttacgctct      1440
tgttacaaca aaggctcgcc actgcccagc taaggtcttc gaaatcgccg ctgaatctct      1500
tgcttccctc gtcaagaagg aggatcacga tcagggcaat cttctcccac cactcaacaa      1560
gatccgtgac tactcattcg gcatcgctta cgatgtttcc aagtacctca tcgacaacga      1620
gctcgcaaca gctgttccac caaagggtac atctctcaag gactggctca aggctcagct      1680
cttcgaacca tcagctgact acgaaccact ttactaagcg cgattttttaa acacttagct      1740 ttcttaattt a                                                           1751

<210> SEQ ID NO 2
<211> LENGTH: 17
<212> TYPE: DNA
<213> ORGANISM: Trichomonas vaginalis

<400> SEQUENCE: 2
tggttgacag ccacttc                                                     17

<210> SEQ ID NO 3
<211> LENGTH: 14
<212> TYPE: DNA
<213> ORGANISM: Trichomonas vaginalis

<400> SEQUENCE: 3
tggcgccgta gatg                                                        14

<210> SEQ ID NO 4
<211> LENGTH: 14
<212> TYPE: DNA
<213> ORGANISM: Trichomonas vaginalis

<400> SEQUENCE: 4
ctctggctct tatg                                                        14

<210> SEQ ID NO 5
<211> LENGTH: 13
<212> TYPE: DNA
<213> ORGANISM: Trichomonas vaginalis

<400> SEQUENCE: 5
tacaggaccg cac                                                         13

<210> SEQ ID NO 6
<211> LENGTH: 19
<212> TYPE: DNA
<213> ORGANISM: Trichomonas vaginalis

<400> SEQUENCE: 6
cctgtaggag gcgttgatg                                                   19

<210> SEQ ID NO 7
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
accaactgtc ggtgaag                                                        17

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagaccgaga atac                                                           14

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
accgcggcat ctac                                                           14

<210> SEQ ID NO 10
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atgtcctggc gtg                                                            13

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
ggacatcctc cgcaactac                                                      19

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gaagattctg gcaagatcaa gga                                                 23

<210> SEQ ID NO 13
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 13
acgacaatgc agcggatgt                                                      19

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
atcctccgca actacccacg cca                                                 23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttacacacca actgtcggtg aag                                                 23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atgtagatgc cgcggtatga t                                                   21

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
ttgccagaag tgggctacac acaccgtc                                            28

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagaggaaac aatgccaatt ctt                                                 23

<210> SEQ ID NO 19
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 19
tgacggtgtg tagcccactt c                                              21

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
acaccaactg tcggtgaagc ttgcc                                          25

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgattccgct ccagacttct cgggaccgcg gcatctac                            38

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
accgcatcga atgactgtct cgggatgtcc tggcgtg                             37

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      probe where the 1st nucleotide positions contains a 6-FAM
      and the 8th position contains Dabcyl

<400> SEQUENCE: 23
tccccgaggg acatcctccg caactac                                        27

<210> SEQ ID NO 24
<211> LENGTH: 244
<212> TYPE: DNA
<213> ORGANISM: Trichomonas vaginalis

<400> SEQUENCE: 24
cacccaccag aggaaacaat gccaattctt tacacaccaa ctgtcggtga agcttgccag    60
aagtgggcta cacaccgtca atcataccgc ggcatctaca tcacaccaga agattctggc   120
aagatcaagg acatcctccg caactaccca cgccaggaca tccgctgcat tgtcgttaca   180
gatgctggcc gtattctcgg tctcggcgat ctcggtgctt ccggccttgg tattccagtt   240
ggta                                                                244
```

ASSAY FOR *TRICHOMONAS VAGINALIS* BY AMPLIFICATION AND DETECTION OF *TRICHOMONAS VAGINALIS* AP65-1 GENE

CROSS REFERENCE TO RELATED APPLICATIONS

The present application is a divisional of U.S. patent application Ser. No. 15/969,216, filed on May 2, 2018, allowed, which application is a continuation of U.S. patent application Ser. No. 14/576,361, filed on Dec. 19, 2014, now issued as U.S. Pat. No. 9,988,692, which is a divisional of U.S. patent application Ser. No. 12/686,695, filed on Jan. 13, 2010, now issued as U.S. Pat. No. 8,945,842, which claims the benefit of the filing date of U.S. Provisional Patent Application No. 61/205,017 filed Jan. 14, 2009, the disclosures of which are incorporated herein by reference.

SEQUENCE LISTING

The instant application contains a Sequence Listing which has been submitted via EFS-Web and is hereby incorporated by reference in its entirety. Said ASCII copy, created on Jan. 5, 2018, is named BECT850.txt, and is 7,899 bytes in size.

BACKGROUND OF THE INVENTION

*Trichomonas vaginalis* is an anaerobic, parasitic flagellated protozoan that is the causative agent of trichomoniasis. It is the most common pathogenic protozoan infection of humans in industrialized countries. It is estimated by the World Health Organization (WHO) that 180 million infections are acquired annually worldwide. The estimates for North America alone are between 5 and 8 million new infections each year, with an estimated rate of asymptomatic cases as high as 50%.

Trichomoniasis is a sexually transmitted disease which can occur in males and females. Symptoms of *T. vaginalis* typically experienced in women include: Vaginitis—itching, burning, and inflammation of the vagina; Cervicitis—inflammation of the cervix; Urethritis—inflammation of the urethra; or a green/yellow, frothy vaginal discharge. In addition, the infection may cause discomfort during intercourse and urination, as well as irritation and itching of the female genital area. In rare cases, lower abdominal pain can occur. Symptoms in women usually appear within 5 to 28 days of exposure.

Most men with trichomoniasis do not exhibit signs or symptoms. Although rare, some men may temporarily have an irritation inside the penis, mild discharge, or slight burning after urination or ejaculation.

There are several known ways to diagnose and detect Trichomoniasis. One classic form of detection is the pap smear, which displays a transparent "halo" around the superficial cell nucleus from samples of infected individuals. However, Trichomoniasis is rarely detected by studying discharge or with a pap smear because of the low sensitivity associated with this form of detection. *T. vaginalis* was traditionally diagnosed via a wet mount, in which "corkscrew" motility was observed. In women, a doctor may collect a specimen during a pelvic examination by inserting a speculum into the vagina and using a cotton-tipped applicator to collect a sample. The sample is then placed onto a microscopic slide and sent to a laboratory for analysis. However, detection via wet mount is less sensitive than newer methods such as rapid antigen testing and transcription-mediated amplification. Huppert et al., CID 2007:45 p. 194. These newer methods have greater sensitivity, but are not in widespread use.

Currently, the most common method of laboratory analysis is via overnight culture of the *T. vaginalis* organism. Sood, et al., Indian J. Med. Res. 125, April 2007, pp. 567-571; Ohlemeyer, et al., Journ. Of Ad. Health, 22:3 pp. 205-208 (March 1998). However, the presence of *T. vaginalis* can also be diagnosed by PCR, using the primers L23861 Fw and Rev. Sichirm, et al., Journ. Of Microbiological Methods, Vol. 68:2, pp. 243-247, (February 2007).

Thus, new diagnostic techniques aimed at more reliably and accurately detecting *T. vaginalis* are desired.

SUMMARY OF THE INVENTION

The adhesion protein gene (i.e. the AP65-1 gene, SEQ ID NO:1), which is about 1.7 kb in length, is present in *T. vaginalis*. The AP65-1 gene has been identified in at least three strains of *T. vaginalis* (ATCC 30001, ATCC 30238, ATCC 300239). It has been unexpectedly determined that a portion of the AP65-1 gene is highly conserved among these three strains of *T. vaginalis* and unique to the *T. vaginalis* organism. Highly conserved, as used herein, means that the identified portion is considered homologous among at least the three above-identified strains. Specifically, the portion of the AP65-1 gene from about base pairs 317 through about 560 is determined to be conserved among the three strains of *T. vaginalis*.

Figure 1A:
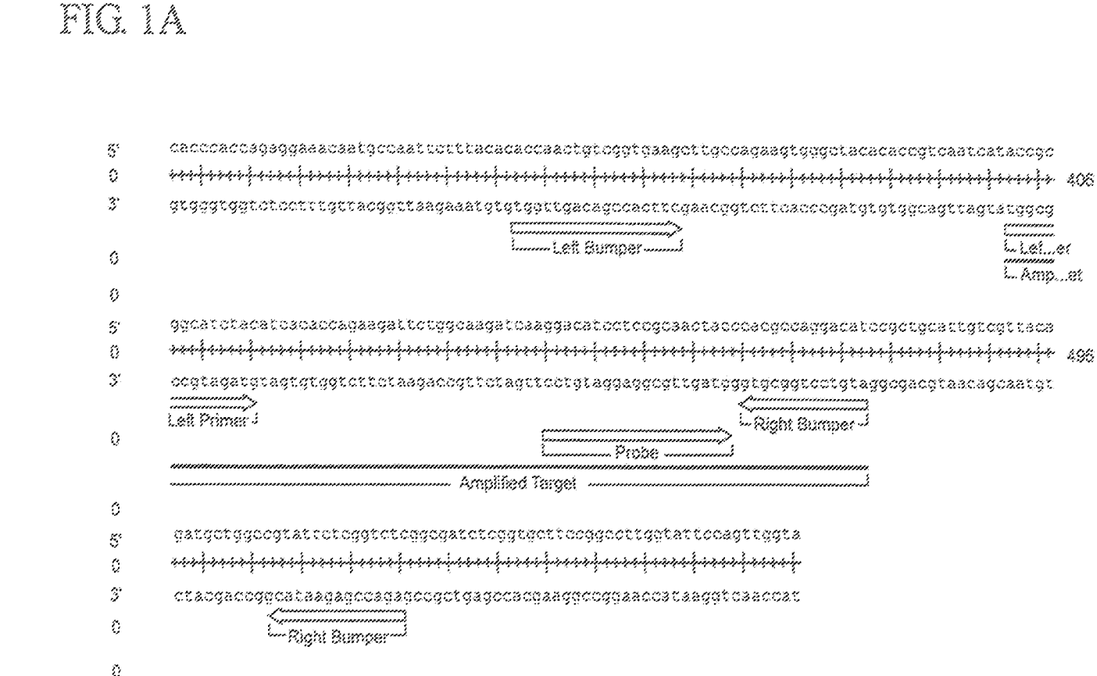
FIG. 1A schematically illustrates an SDA probe set and the target binding sites to which the probes attach in the portion of the AP65-1 gene (SEQ ID NO: 24)
Figure 1B:
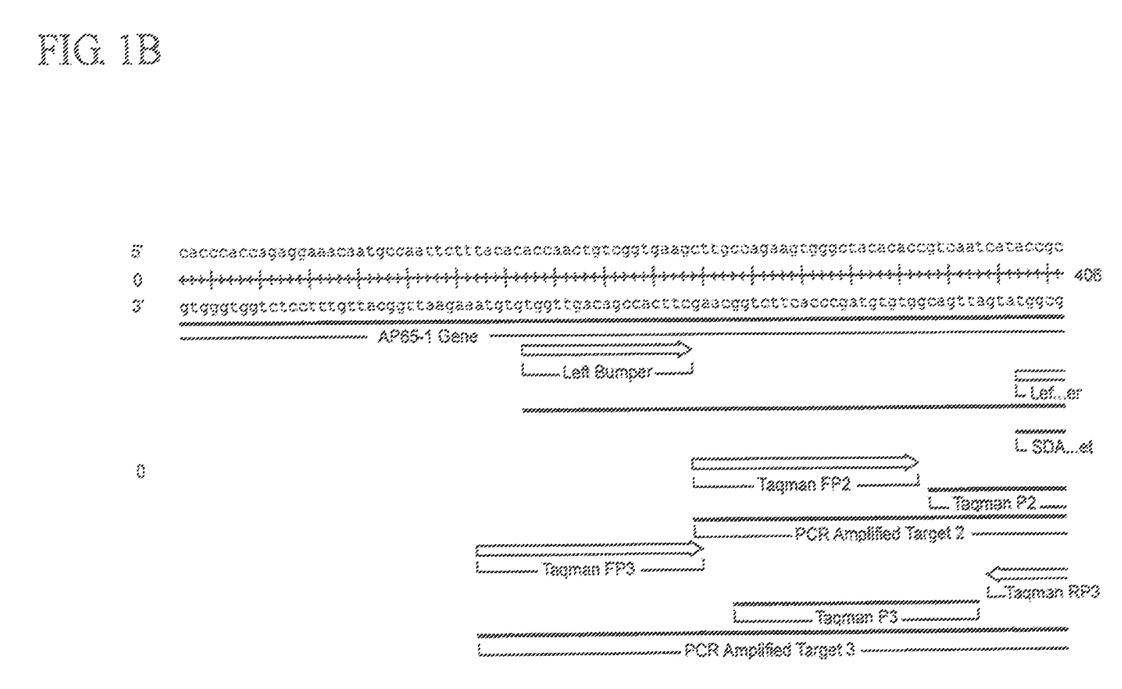
FIG. 1B illustrates three Taqman® probe sets and the target binding sites to which the probes attach in the portion of the AP65-1 gene (SEQ ID NO: 24).

Oligonucleotides described herein are used to detect the presence of *T. vaginalis* using the AP65-1 gene. Specifically, oligonucleotides described herein select for certain portions of the AP65-1 gene and amplify portions thereof for detection. More specifically, the oligonucleotides described herein are used to select for and amplify one or more portions of the AP65-1 nucleic acid sequence within the organism as a mechanism to detect *T. vaginalis*. Even more specifically, the oligonucleotides described herein target the conserved portion (base pairs 317 to 560 of Genbank Accession U18346) of the *T. vaginalis* AP65-1 gene. The target portion of the AP65-1 gene is illustrated in FIGS. 1A and 1B.

Oligonucleotide probe sets described herein are designed to select for the AP65-1 gene and offer a mechanism for detection. The probe set design is based upon a number of factors, chief among which is the assay in which the probe set is used. Assays for the detection of DNA or RNA sequences are well known in the art. These assays typically use some type of amplification or some type of imaging to confirm the presence of the target DNA. Examples of amplification reactions include PCR (polymerase chain reaction), SDA (strand displacement amplification), TMA (transcription mediated amplification) and LCR (ligase chain reaction).

In one embodiment, the amplification mechanism selected for detection is SDA. SDA is an isothermal amplification mechanism and therefore does not involve thermal cycling. As such, SDA probe sets are designed for a target melting temperature ($T_m$) within a predetermined narrow range. Target melting temperature ($T_m$) is the temperature at which at least fifty percent of the oligonucleotide is annealed to its perfect complement. One skilled in the art is aware that the $T_m$ of an oligonucleotide sequence is determined by the number of base pairs in the sequence as well as the type of bases in the sequence. These guidelines for designing oligonucleotides are well know to one skilled in the art and are not set forth in detail herein.

It is advantageous if the target site within the AP65-1 gene used in conjunction with the oligonucleotides described herein does not have long stretches of repeated bases. That is, no more than 3 or 4 bases in the sequence are the same base. Minimizing the number of base repetitions permits a system design with optimal melting temperatures for the oligonucleotides. Furthermore, the oligonucleotides that bind to those discrete portions of the AP65-1 gene will not interact with each other when placed within close proximity.

Suitable binding sites on the AP65-1 gene for one embodiment of an SDA probe set are listed in the following Table 1 along with their location on the conserved portion of the AP65-1 gene.

TABLE 1

| SEQUENCE | Location* | SEQ ID Number |
|---|---|---|
| TGGTTGACAGCCACTTC | 352-368 | SEQ ID NO: 2 |
| TGGCGCCGTAGATG | 402-415 | SEQ ID NO: 3 |
| CTCTGGCTCTTATG | 507-520 | SEQ ID NO: 4 |
| TACAGGACCGCAC | 465-477 | SEQ ID NO: 5 |
| CCTGTAGGAGGCGTTGATG | 445-463 | SEQ ID NO: 6 |

*Genbank Accession No. U18346

The oligonucleotide SDA probe sets described herein are sufficiently complementary to portions of the AP65-1 gene so that they selectively bind to those portions.

For the SDA embodiment described herein, the oligonucleotide probe set has left and right bumper primers, left and right amplification primers and a probe. In a preferred embodiment these primers and probes have oligonucleotide sequences that are the perfect complement to the sequences described above. Specifically, the left and right bumper primers have the sequences ACCAACTGTCGGTGAAG (SEQ ID NO:7) and GAGACCGAGAATAC (SEQ ID NO:8) respectively. SEQ ID NO:7 is the perfect complement of SEQ ID NO:2 and SEQ ID NO:8 is the perfect complement of SEQ ID NO:4. The left and right primers contain the respective sequences ACCGCGGCATCTAC (SEQ ID NO:9) and ATGTCCTGGCGTG (SEQ ID NO:10). SEQ ID NO:9 is the perfect complement to SEQ ID NO:3. SEQ ID NO:10 is the perfect complement of SEQ ID NO:5. The SDA probe set also includes an oligonucleotide probe that has a sequence GGACATCCTCCGCAACTAC (SEQ ID NO:11) which is the perfect complement of SEQ ID NO:6. One skilled in the art will appreciate that less than perfect complementarity is required as long as the $T_m$ requirements and other assays conditions are met.

The primers and probe have additional nucleotides attached thereto. The probe also has additional imaging moieties affixed thereto. These moieties facilitate the detection of the target DNA sequence. Using this oligonucleotide probe set, an SDA assay may be performed on a sample in order to determine the presence or absence of all three strains of *T. vaginalis*. In one illustrative embodiment, about a 75 base pair region of the AP65-1 gene is amplified between about base pair 317 and 560. Even more specifically, the 75 base pair region of the AP65-1 gene is amplified between base pairs 402 and 477.

In an alternative embodiment, the amplification mechanism selected for detection is Taqman® real-time PCR assay. Oligonucleotide sequences bind to the AP65-1 gene region between about base pair 317 to about base pair 560. Primer/probe sets are configured to not only selectively bind in this region of the AP65-1 gene, but to amplify some portion of the AP65-1 gene sequence for detection. The oligonucleotides described herein have a sequence that is capable of binding to the target nucleic acid sequence (and its complementary strand). The oligonucleotides described herein may also be used, either alone or in combination, to facilitate detection through amplification of AP65-1 gene nucleic acid sequence. Examples of three probes sets used for Taqman® real-time PCR assays, described in terms of their oligonucleotide sequences, are:

TABLE 2

| Probe description: | Oligonucleotide 5' Sequence 3' |
|---|---|
| AP65-1 Taqman® Forward Primer 1 | GAAGATTCTGGCAAGATCAAGGA (SEQ ID NO: 12) |
| AP65-1 Taqman® Reverse Primer 1 | ACGACAATGCAGCGGATGT (SEQ ID NO: 13) |
| AP65-1 gene Taqman® Probe 1 | ATCCTCCGCAACTACCCACGCCA (SEQ ID NO: 14) |
| AP65-1 gene Taqman® Forward Primer 2 | TTACACACCAACTGTCGGTGAAG (SEQ ID NO: 15) |
| AP65-1 gene Taqman® Reverse Primer 2 | ATGTAGATGCCGCGGTATGAT (SEQ ID NO: 16) |
| AP65-1 gene Taqman® Probe 2 | TTGCCAGAAGTGGGCTACACACACCGTC (SEQ ID NO: 17) |
| AP65-1 gene Taqman® Forward Primer 3 | CAGAGGAAACAATGCCAATTCTT (SEQ ID NO: 18) |
| AP65-1 gene Taqman® Reverse Primer 3 | TGACGGTGTGTAGCCCACTTC (SEQ ID NO: 19) |
| AP65-1 gene Taqman® Probe 3 | ACACCAACTGTCGGTGAAGCTTGCC (SEQ ID NO: 20) |

In yet another embodiment, the oligonucleotides may be used in a method for detecting the presence or absence of *T. vaginalis* in a sample. In a further embodiment, the method includes treating a sample using one or more oligonucleotides specific for the target sequence in a nucleic acid amplification reaction and detecting the presence or absence of the amplified nucleic acid product.

In one illustrative embodiment SDA is selected as the amplification reaction. In the context of this embodiment, the oligonucleotides described herein as suited for use in the SDA assay are used in combination as amplification primers, bumper primers and a detector in that assay.

In another embodiment, a kit is provided for the detection of *T. vaginalis*. The kit includes one or more of the oligonucleotides described herein that selectively bind to the AP65-1 gene of *T. vaginalis* and are capable of amplifying a target sequence that may be used for detection of that organism. The kit is provided with one or more of the oligonucleotides and buffer reagents for performing amplification assays.

In one aspect of the kit, oligonucleotides and reagents for purposes of SDA may be provided. In this aspect, two oligonucleotides are provided as amplification primers, two oligonucleotides are provided as bumper primers and one oligonucleotide may be provided for use as a detector.

In yet another aspect of the kit, the oligonucleotides for SDA purposes may be provided in dried or liquid format. In dried format, the composition may be applied to an appropriate receptacle where sample and proper SDA buffers may be added to perform the assay.

In yet another aspect of the kit, oligonucleotides and reagents for purposes of Taqman® PCR may be provided. In this aspect, three oligonucleotides are provided. Two of the three are amplification primers and the third oligonucleotide is configured as a detector.

DETAILED DESCRIPTION OF THE INVENTION

Described herein is a method of detecting *Trichomonas vaginalis* using an assay that consists of one or more oligonucleotide probes that bind to the AP65-1 gene. Applicant has determined that a region of the AP65-1 gene among at least three strains of *T. vaginalis* (ATCC 30001, ATCC 30238 and ATCC 300239) is highly conserved. That is, a region of the AP65-1 gene is sufficiently homologous among the three *T. vaginalis* strains so that the oligonucleotide probes are capable of binding to the identified region of the AP65-1 gene for all three strains. It is also contemplated that the oligonucleotide probes are capable of binding to a corresponding region of the AP65-1 gene in other *T. vaginalis* strains.

The oligonucleotides described herein bind to a region of the AP65-1 gene. Specifically, the oligonucleotides described herein target the region of base pairs 317 to 560 of the AP65-1 gene. The region of base pairs 317 to 560 of the AP65-1 gene has been observed among three strains of *T. vaginalis* (ATCC 30001, ATCC 30238 and ATCC 300239) and identified as highly conserved among at least these three strains. The invention exploits this conserved region and the stability of the AP65-1 gene among at least three strains of *T. vaginalis*.

The AP65-1 gene is believed to be unique to *T. vaginalis*. Due to the conservation and stability of this gene generally, the invention can minimize or eliminate cross reacting/detecting other organisms. The conservation and stability between base pairs 317 to 560 of the AP65-1 gene advantageously do not appear to demonstrate homology with other parasitic organisms, which allows use of this region of the AP65-1 gene for specific detection of *T. vaginalis* and reduces the risk of false positives.

The AP65-1 gene belongs to the AP65 (adhesion protein 65) multigene family encoding multiple homologous 65-kDa proteins whose protein sequences are identical to those of the hydrogenosomal malic enzymes. These proteins have also been detected on plasma membranes as part of adhesion complexes during host-parasite encounters. Without being bound by any theory Applicant believes that the AP65-1 gene encodes proteins associated with a receptor on *T. vaginalis* that allows it to bind a target site on its host. As such, it believed the AP65-1 gene plays a significant role in the pathogenicity of *T. vaginalis*.

Thus, because the AP65-1 gene may play a role in pathogenicity and it is stable/conserved, it is advantageous to use for detection of *T. vaginalis*. The disclosed oligonucleotides are designed to detect the AP65-1 gene because the likelihood of cross reaction/detection with other organisms or eukaryotic cell that could be found in the patient's sample is minimal.

The oligonucleotide probes and probes sets described herein are specifically designed to target the AP65-1 gene nucleic acid, and may be used for detecting *T. vaginalis*. More specifically, the oligonucleotides target the conserved portion of the *T. vaginalis* AP65-1 gene. The embodiments described herein provide oligonucleotides that select for a nucleic acid sequence in *T. vaginalis*.

The probe sets provide a detectable signal when the area targeted by the oligonucleotides is present in the sample. This is a highly reliable indication of the presence of the AP65-1 gene and, in turn, is a highly reliable indication for *Trichomonas vaginalis*.

In the preferred embodiments, the oligonucleotide probes and probe sets are configured to assay for the AP65-1 gene using DNA sequence detection. Often times, detection assays involve the use of amplification or imaging to confirm the presence of DNA. Such reactions include SDA, tSDA or homogeneous real time fluorescent tSDA. These methods are known to those skilled in the art from references such as U.S. Pat. Nos. 5,547,861 and 5,648,211, 5,928,869 and 5,846,726 the disclosures of which are hereby incorporated herein by reference. Other methods such as PCR (e.g. Taqman® PCR), TMA, and LCR may also be used. Further, a kit for detecting *T. vaginalis* is disclosed.

The oligonucleotides as described herein target the AP65-1 gene contained within *T. vaginalis*. The AP65-1 gene is known in the art and its sequence is about 1.7 kb in length. See Genbank Accession Number U18346.

One such probe set, specifically designed for the SDA assay, is presented in Table 3 below.

TABLE 3

| SEQ ID | Description | Oligonucleotide Sequence 5'-3' | ~Tm (° C.) | ORF Location* (bp) |
|---|---|---|---|---|
| SEQ ID NO: 7 | Left Bumper (upstream) | ACCAACTGTCGGTGAAG | 52 | 352-368 |
| SEQ ID NO: 21 | Left Primer (upstream) | CGATTCCGCTCCAGACTTCTCGGGACCGCGGCATCTAC | 46 | 402-415 |
| SEQ ID NO: 8 | Right Bumper (downstream) | GAGACCGAGAATAC | 42 | 507-520 |
| SEQ ID NO: 22 | Right Primer (downstream) | ACCGCATCGAATGACTGTCTCGGGATGTCCTGGCGTG | 42 | 465-477 |
| SEQ ID NO: 23 | Probe-detector | (6-Fam)-TCCCCGAG(dT)-Dabcyl<u>GGACATCCTCCGCAACTAC</u> | 60 | 445-463 |

*Genbank Accession U18346

The left bumper oligonucleotide (ACCAACTGTCGGT-GAAG; SEQ ID NO:7) may hybridize to a complementary target sequence contained within the AP65-1 gene. More specifically, left bumper binds to the location at about 352-368 base pairs of the AP65-1 gene. This oligonucleotide sequence was specifically designed to bind to this particular region of the AP65-1 gene.

The left primer oligonucleotide includes SEQ ID NO:9 (ACCGCGGCATCTAC) and may hybridize to a complementary target sequence contained within the AP65-1 gene. More specifically, left primer binds to the location at about 402-415 base pairs of the AP65-1 gene. The left primer was specifically designed to bind to this particular region of the AP65-1 gene.

The right bumper oligonucleotide (GAGACCGAGAATAC; SEQ ID NO:8) may hybridize to a complementary target sequence contained within the AP65-1 gene. More specifically the AP65-1 gene right bumper binds to the location at about 507-520 base pairs of the AP65-1 gene. This oligonucleotide sequence was designed to bind this particular region of the AP65-1 gene.

The right primer oligonucleotide contains SEQ ID NO:10 (ATGTCCTGGCGTG) and may hybridize to a complementary target sequence contained within the AP65-1 gene. More specifically, the right primer binds to the location at about 465-477 base pairs of the AP65-1 gene.

The oligonucleotide probe that contains SEQ ID NO:11 (GGACATCCTCCGCAACTAC) was designed to specifically bind to base pairs 445-463 of the AP65-1 gene.

The probes described above are described in terms of being 100% complementary to their target binding sequences. As described below, primers and probes can bind to target sequences even though they are less than 100% complementary with those regions. The requisite degree of complementarity depends on a variety of factors including the stringency of the binding conditions. Depending upon the stringency conditions employed, the primers and probes may be modified to include different bases in their sequence and still be sufficiently complementary to bind to the target region of the AP65-1 nucleic acid. Sufficiently complementary, as used herein include complementarity of 70% or more. In preferred embodiments, the complementarity of the primers/probes to their target sequence is at least 80% over the length of the binding portion of the primers/probes. More preferably, the complementarity of the primers and probes to their target sequences is 90% or more.

While the oligonucleotides described herein must be sufficiently complementary to bind their respective portions of the AP65-1 nucleic acid, it is recognized at some point the sequence of the oligonucleotide becomes less complementary to the sequence in the AP65-1 nucleic acid and may bind other nucleic acid sequences. Therefore, it is desirable that the oligonucleotide probes remain sufficiently complementary with its respective portion of the AP65-1 gene, and not lose selectivity for its respective target binding site.

The oligonucleotide probe set described above is configured for use in SDA. However, it is understood that with routine experimentation, one of skill in the art may use the oligonucleotide sequences described herein with or without modification as probes for use in other assays.

The oligonucleotides described herein may be used to amplify a nucleic acid sequence within the target region of the AP65-1 gene. In addition, any sequence which may be produced as a result of an amplification reaction, referred to as amplification products, amplimers, or amplicons, may serve as amplifiable target sequence for the oligonucleotides described herein.

In the context of SDA, the oligonucleotide probe set as described may amplify a 75 base pair portion of the AP65-1 gene. Thus, oligonucleotides may amplify a naturally occurring AP65-1 nucleic acid sequence, the complementary second strand of the naturally occurring AP65-1 gene nucleic acid sequence, and either strand of a copy of the natural occurring AP65-1 gene sequence, which may be produced as a result of an amplification reaction.

An amplification primer is generally used for amplifying a target sequence by extension of the primer after hybridization to the target sequence. Amplification primers are typically about 10-75 nucleotides in length, preferably about 15-50 nucleotides in length. The total length of an amplification primer for use in SDA is typically about 25-50 nucleotides.

An amplification primer of one embodiment of the invention as described herein is useful for SDA and generally has three types of sequences. One sequence, a target binding sequence, within the primer may be capable of binding or hybridizing to the target sequence. Another sequence within the primer may be a recognition site for a restriction endonuclease. Yet another sequence within the primer may act as a repriming sequence.

The target binding sequence within the oligonucleotide amplification primer may generally be located at its 3' end. The target binding sequence may be about 10-25 nucleotides in length and may have hybridization specificity to the amplification primer. Thus, it is understood that one skilled in the art may change the target binding sequence to effectively change hybridization specificity of the amplification primer and direct hybridization to an alternative sequence.

An SDA amplification primer may also have a recognition site for a restriction endonuclease 5' to the target binding sequence. The recognition site on the amplification primer may allow for a restriction endonuclease to nick one strand of a DNA duplex when the recognition site is hemimodified. This is described by G. Walker, et al. (1992. PNAS 89:392-396 and 1992 NucL Acids Res. 20:1691-1696). The nucleotides 5' to the restriction endonuclease recognition site (the "tail") function as a polymerase repriming site when the remainder of the amplification primer is nicked and displaced during SDA.

The repriming function of the tail nucleotides sustains the SDA reaction and may allow synthesis of multiple amplicons from a single target molecule. The tail is generally about 10-25 nucleotides in length. Its length and sequence are generally not critical and can be routinely selected and modified. As the target binding sequence is the portion of a primer which determines its target-specificity, for amplification methods which do not require specialized sequences at the ends of the target the amplification primer generally consists essentially of only the target binding sequence. For amplification methods which require specialized sequences appended to the target other than the nickable restriction endonuclease recognition site and the tail for SDA (e.g., an RNA polymerase promoter for 3SR, NASBA or transcription based amplification), may require specialized sequences to link the target binding sequence. This may be accomplished using routine methods for preparation of oligonucleotides without altering the hybridization specificity of the primer.

Table 3 depicts two oligonucleotides useful as amplification primers in the context of SDA. Those amplification primers, the left primer and right primer, are shown with target binding sequences, underlined. These portions may hybridize to a target sequence of the AP65-1 gene. The bold sequences indicate a restriction enzyme site. The sequence without any markings may act as the tail region.

A bumper primer or external primer is a primer used to displace primer extension products in isothermal amplification reactions. The bumper primer may anneal to a target sequence upstream of the amplification primer such that extension of the bumper primer may displace the downstream amplification primer and its extension product. Two oligonucleotides, the left bumper and right bumper, described in Table 3 may be useful as bumper primers in the context of SDA. Table 3 also describes the SDA probe/detector. The positions of hybridization of the probes described in Table 3 to the AP65-1 gene when used in an SDA context are depicted in FIG. 1.

The target sequence produced by hybridization of a primer and extension of the primer by polymerase using the target sequence template may be referred to as the extension product for purposes of discussion herein.

In one embodiment, an SDA system was designed that comprises direct detection using a linear detector probe format. The SDA amplicon size is approximately 80 base pairs long and contains no BsoB I sites. Oligo 6.0 software was used to ensure that no significant secondary structure or interactions between oligonucleotides exist that would negatively affect SDA performance. Each of the oligos in the T. vaginalis SDA design was checked using the NCBI site (Blast) and none showed significant homology with any relevant organism expected to be isolated from a genitourinary specimen. Thus, cross-reactivity is expected to be minimal, if any, with other organisms expected to be isolated from a genitourinary specimen.

It is understood to one skilled in the art that the oligonucleotides as used in amplification assays may be modified to some extent without loss of utility or specificity towards a target sequence in T. vaginalis, for example, the AP65-1 gene. For example, as is known in the art, hybridization of complementary and partially complementary nucleic acid sequences may be obtained by adjustment of the hybridization conditions to increase or decrease stringency (i.e., adjustment of hybridization temperature or salt content of the buffer). Such minor modifications of the disclosed sequences and any necessary adjustments of hybridization conditions to maintain T. vaginalis—specificity require only routine experimentation and are within the ordinary skill in the art.

As a general guide in designing oligonucleotides useful as primers, Tm decreases approximately 1° C.-1.5° C. with every 1% decrease in sequence homology. Temperature ranges may vary between about 50° C. and 62° C., but the amplification primers may be designed to be optimal at 52° C. However, temperatures below 50° C. may result in primers lacking specificity, while temperatures over 62° C. may result in no hybridization. A further consideration when designing amplification primers may be the guanine and cytosine content. Generally, the GC content for a primer may be about 60-70%, but may also be less and can be adjusted appropriately by one skilled in the art. The hybridizing region of the target binding sequence may have a Tm of about 42° C.-48° C. Annealing complementary and partially complementary nucleic acid sequences may be obtained by modifying annealing conditions to increase or decrease stringency (i.e., adjusting annealing temperature or salt content of the buffer). Modifications such as those to the disclosed sequences and any necessary adjustments of annealing conditions to maintain AP65-1 gene specificity require only routine experimentation and are within the ordinary skill in the art.

The amplification products generated using the inventive primers may be detected by a characteristic size, for example on polyacrylamide or agarose gels stained with ethidium bromide. Alternatively, amplified T. vaginalis AP65-1 gene target sequence may be detected by means of an assay probe, which is an oligonucleotide tagged with a detectable label. In one embodiment, at least one tagged assay probe may be used for detection of amplified target sequences by hybridization (a detector probe), by hybridization and extension as described by Walker, et al., Nucl. Acids Rev., supra (a detector primer) or by hybridization, extension and conversion to double stranded form as described in EP 0 678 582 (a signal primer). Preferably, the assay probe is selected to hybridize to a sequence in the target which is between the amplification primers, i.e., it should be an internal assay probe. Alternatively, an amplification primer sequence or the target binding sequence thereof may be used as the assay probe.

The detectable label of the assay probe may be a moiety which can be detected either directly or indirectly as an indication of the presence of the target nucleic acid. For direct detection of the label, assay probes may be tagged with a radioisotope and detected by autoradiography or tagged with a fluorescent moiety and detected by fluorescence as is known in the art. Alternatively, the assay probes may be indirectly detected by tagging with a label which requires additional reagents to render it detectable. Indirectly detectable labels include, for example, chemiluminescent agents, enzymes which produce visible reaction products and ligands (e.g., haptens, antibodies or antigens) which may be detected by binding to labeled specific binding partners (e.g., antibodies or antigens/haptens). Ligands are also useful for immobilizing the ligand-labeled oligonucleotide (the capture probe) on a solid phase to facilitate its detection. Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to or including such labels in, oligonucleotides are well known in the art and any of these methods are suitable for use in the invention described herein.

Examples of specific detection methods which may be employed include a chemiluminescent method in which amplified products are detected using a biotinylated capture probe and an enzyme-conjugated detector probe as described in U.S. Pat. No. 5,470,723. After hybridization of these two assay probes to different sites in the assay region of the target sequence (between the binding sites of two amplification primers), the complex may be captured on a streptavidin-coated microtiter plate by means of the capture probe, and the chemiluminescent signal is developed and read in a luminometer. As another alternative for detection of amplification products, a signal primer as described in EP 0 678 582 may be included in the SDA reaction. In this embodiment, labeled secondary amplification products are generated during SDA in a target amplification-dependent manner and may be detected as an indication of target amplification by means of the associated label.

Oligonucleotide hybridization may be species-specific. That is, detection, amplification or oligonucleotide hybridization in a species of organism or a group of related species may occur without substantial detection, amplification or oligonucleotide hybridization in other species of the same genus or species of a different genus. Oligonucleotides disclosed herein may be useful for identification of all three strains of *T. vaginalis*. This includes strains 286, 272 and IR78.

Other sequences, as required for performance of a selected amplification reaction, may optionally be added to the target binding sequences disclosed herein without altering the species-specificity of the oligonucleotide. By way of example, the *T. vaginalis* AP65-1-specific amplification primers of the invention may contain a recognition site for the restriction endonuclease BsoBI which is nicked during the SDA reaction.

It will be apparent to one skilled in the art that other nickable restriction endonuclease recognition sites may be substituted for the BsoBI recognition site, including but not limited to those recognition sites disclosed in EP 0 684 315. Preferably, the recognition site is for a thermophilic restriction endonuclease so that the amplification reaction may be performed under the conditions of thermophilic SDA (tSDA). Similarly, the tail sequence of the amplification primer (5' to the restriction endonuclease recognition site) is generally not critical, although the restriction site used for SDA and sequences which will hybridize either to their own target binding sequence or to the other primers should be avoided.

Some amplification primers for SDA according to the invention therefore consist of 3' target binding sequences, a nickable restriction endonuclease recognition site 5' to the target binding sequence and a tail sequence about 10-25 nucleotides in length 5' to the restriction endonuclease recognition site. The nickable restriction endonuclease recognition site and the tail sequence are sequences required for the SDA reaction. For other amplification reactions, the amplification primers according to the invention may consist of the disclosed target binding sequences only (e.g., for PCR) or the target binding sequence and additional sequences required for the selected amplification reaction (e.g., sequences required for SDA as described above or a promoter recognized by RNA polymerase for 3SR).

In SDA, the bumper primers are not essential for species-specificity, as they function to displace the downstream, species-specific amplification primers. It is only required that the bumper primers hybridize to the target upstream from the amplification primers so that when they are extended they will displace the amplification primer and its extension product. The particular sequence of the bumper primer is therefore generally not critical, and may be derived from any upstream (to left amplification primer) or downstream (to right amplification primer) target sequence which is sufficiently close to the binding site of the amplification primer to allow displacement of the amplification primer extension product upon extension of the bumper primer. Occasional mismatches with the target in the bumper primer sequence or some cross-hybridization with non-target sequences do not generally negatively affect amplification efficiency as long as the bumper primer remains capable of hybridizing to the specific target sequence. However, the bumper primers described herein are species-specific for *T. vaginalis* and may therefore also be used as target binding sequences in amplification primers, if desired.

Amplification reactions employing the primers described herein may incorporate thymine as taught by Walker, et al., supra, or they may wholly or partially substitute 2'-deoxyuridine 5'-triphosphate for TTP in the reaction to reduce cross-contamination of subsequent amplification reactions, e.g., as taught in EP 0 624 643. dU (uridine) is incorporated into amplification products and can be excised by treatment with uracil DNA glycosylase (UDG). These basic sites render the amplification product not amplifiable in subsequent amplification reactions. UDG may be inactivated by uracil DNA glycosylase inhibitor (Ugi) prior to performing the subsequent amplification to prevent excision of dU in newly-formed amplification products.

Other systems may be used for performing tSDA using different combinations of primers, bumpers and detectors. Such systems are well known to one skilled in the art and not discussed in detail herein.

A primer mix may be prepared to contain an upstream primer and downstream primer. The primer mix also contains the upstream and downstream bumpers. The primers and bumpers may be used at final concentrations of about 0.5 and 0.05 uM, respectively.

Oligonucleotide(s) used to facilitate detection or identification of a nucleic acid may be used as an assay probe. For example, in the invention described herein, assay probes may be used for detection or identification of *T. vaginalis* AP65-1 nucleic acids. Detector probes, detector primers, capture probes and signal primers as described below are examples of assay probes.

The primers and probes are preferably used in a tSDA real time fluorescence energy transfer method. Strand Displacement Amplification (SDA) is an isothermal method of nucleic acid amplification in which extension of primers, nicking of a hemimodified restriction endonuclease recognition/cleavage site, displacement of single stranded extension products, annealing of primers to the extension products (or the original target sequence) and subsequent extension of the primers occurs concurrently in the reaction mix. This is in contrast to polymerase chain reaction (PCR), in which the steps of the reaction occur in discrete phases or cycles as a result of the temperature cycling characteristics of the reaction. SDA is based upon 1) the ability of a restriction endonuclease to nick the unmodified strand of a hemiphosphorothioate form of its double stranded recognition/cleavage site and 2) the ability of certain polymerases to initiate replication at the nick and displace the downstream non-template strand. After an initial incubation at increased temperature (about 95° C.) to denature double stranded target sequences for annealing of the primers, subsequent polymerization and displacement of newly synthesized strands takes place at a constant temperature.

Production of each new copy of the target sequence consists of five steps: 1) binding of amplification primers to an original target sequence or a displaced single-stranded extension product previously polymerized, 2) extension of the primers by a 5'-3' exonuclease deficient polymerase incorporating an a-thio deoxynucleoside triphosphate (a-thio dNTP), 3) nicking of a hemimodified double stranded restriction site, 4) dissociation of the restriction enzyme from the nick site, and 5) extension from the 3' end of the nick by the 5'-3' exonuclease deficient polymerase with displacement of the downstream newly synthesized strand. Nicking, polymerization and displacement occur concurrently and continuously at a constant temperature because extension from the nick regenerates another nickable restriction site.

When a pair of amplification primers is used, each of which hybridizes to one of the two strands of a double stranded target sequence, amplification is exponential. This is because the sense and antisense strands serve as templates for the opposite primer in subsequent rounds of amplification. When a single amplification primer is used, amplification is linear because only one strand serves as a template for primer extension. Examples of restriction endonucleases which nick their double stranded recognition/cleavage sites when an a-thio dNTP is incorporated are HincII, HindII, AvaI, NciI and Fnu4HI. All of these restriction endonucleases and others which display the required nicking activity are suitable for use in conventional SDA. However, they are relatively thermo labile and lose activity above about 40° C.

Targets for amplification by SDA may be prepared by fragmenting larger nucleic acids by restriction with an endonuclease which does not cut the target sequence. However, it is generally preferred that target nucleic acids having the selected restriction endonuclease recognition/cleavage sites for nicking in the SDA reaction be generated as described by Walker, et al. (1992, Nuc. Acids Res., supra) and in U.S. Pat. No. 5,270,184 (hereby incorporated by reference). Briefly, if the target sequence is double stranded, four primers are hybridized to it. Two of the primers (S1 and S2) are SDA amplification primers and two (B1 and B2) are external or bumper primers. S1 and S2 bind to opposite strands of double stranded nucleic acids flanking the target sequence. B1 and B2 bind to the target sequence 5' of S1 and S2, respectively. The exonuclease deficient polymerase is then used to simultaneously extend all four primers in the presence of three deoxynucleoside triphosphates and at least one modified deoxynucleoside triphosphate (e.g., 2'-deoxyadenosine 5'-O-(1-thiotriphosphate), "dATP a S"). The extension products of S1 and S2 are thereby displaced from the original target sequence template by extension of B1 and B2. The displaced, single stranded extension products of the amplification primers serve as targets for binding of the opposite amplification and bumper primer (e.g., the extension product of S1 binds S2 and B2). The next cycle of extension and displacement results in two double stranded nucleic acid fragments with hemimodified restriction endonuclease recognition/cleavage sites at each end. These are suitable substrates for amplification by SDA. As in SDA, the individual steps of the target generation reaction occur concurrently and continuously, generating target sequences with the recognition/cleavage sequences at the ends required for nicking by the restriction enzyme in SDA. As all of the components of the SDA reaction are already present in the target generation reaction, target sequences generated automatically and continuously enter the SDA cycle and are amplified.

To prevent cross-contamination of one SDA reaction by the amplification products of another, dUTP may be incorporated into SDA-amplified DNA in place of dTTP without inhibition of the amplification reaction. The uracil-modified nucleic acids may then be specifically recognized and inactivated by treatment with uracil DNA glycosylase (UDG). Therefore, if dUTP is incorporated into SDA-amplified DNA in a prior reaction, any subsequent SDA reactions can be treated with UDG prior to amplification of double stranded targets, and any dU containing DNA from previously amplified reactions will be rendered not amplifiable. The target DNA to be amplified in the subsequent reaction does not contain dU and will not be affected by the UDG treatment. UDG may then be inhibited by treatment with Ugi prior to amplification of the target. Alternatively, UDG may be heat-inactivated. In thermophilic SDA, the higher temperature of the reaction itself 50° C.) can be used to concurrently inactivate UDG and amplify the target.

SDA requires a polymerase which lacks 5'-3' exonuclease activity, initiates polymerization at a single stranded nick in double stranded nucleic acids, and displaces the strand downstream of the nick while generating a new complementary strand using the unnicked strand as a template. The polymerase must extend by adding nucleotides to a free 3'-OH. To optimize the SDA reaction, it is also desirable that the polymerase be highly processive to maximize the length of target sequence which can be amplified. Highly processive polymerases are capable of polymerizing new strands of significant length before dissociating and terminating synthesis of the extension product. Displacement activity is essential to the amplification reaction, as it makes the target available for synthesis of additional copies and generates the single stranded extension product to which a second amplification primer may hybridize in exponential amplification reactions. Nicking activity is also of great importance, as it is nicking which perpetuates the reaction and allows subsequent rounds of target amplification to initiate.

Thermophilic SDA is performed essentially as the conventional SDA described by Walker, et al. (1992, PNAS and Nuc. Acids Res., supra), with substitution of the desired thermostable polymerase and thermostable restriction endonuclease. Of course, the temperature of the reaction will be adjusted to the higher temperature suitable for the substituted enzymes and the HincII restriction endonuclease recognition/cleavage site will be replaced by the appropriate restriction endonuclease recognition/cleavage site for the selected thermostable endonuclease. Also in contrast to Walker, et al., the practitioner may include the enzymes in the reaction mixture prior to the initial denaturation step if they are sufficiently stable at the denaturation temperature. Preferred restriction endonucleases for use in thermophilic SDA are BsrI, BstNI, BsmAI, BslI and BsoBI (New England BioLabs), and BstOI (Promega). The preferred thermophilic polymerases are Bca (Panvera) and Bst (New England Biolabs).

Homogeneous real time fluorescent tSDA is a modification of tSDA. It employs detector oligonucleotides to produce reduced fluorescence quenching in a target-dependent manner. The detector oligonucleotides contain a donor/acceptor dye pair linked such that fluorescence quenching occurs in the absence of target. Unfolding or linearization of an intramolecularly base-paired secondary structure in the detector oligonucleotide in the presence of the target increases the distance between the dyes and reduces fluorescence quenching. Unfolding of the base-paired secondary structure typically involves intermolecular base-pairing between the sequence of the secondary structure and a complementary strand such that the secondary structure is at least partially disrupted. It may be fully linearized in the presence of a complementary strand of sufficient length. In a preferred embodiment, a restriction endonuclease recognition site (RERS) is present between the two dyes such that intermolecular base-pairing between the secondary structure and a complementary strand also renders the RERS double-stranded and cleavable or nickable by a restriction endonuclease. Cleavage or nicking by the restriction endonuclease separates the donor and acceptor dyes onto separate nucleic acid fragments, further contributing to decreased quenching. In either embodiment, an associated change in a fluorescence parameter (e.g., an increase in donor fluorescence intensity, a decrease in acceptor fluorescence intensity or a ratio of fluorescence before and after unfolding) is monitored as an indication of the presence of the target sequence. Monitoring a change in donor fluorescence intensity is preferred, as this change is typically larger than the change in acceptor fluorescence intensity. Other fluorescence parameters such as a change in fluorescence lifetime may also be monitored.

A detector oligonucleotide for homogeneous real time fluorescent tSDA is an oligonucleotide which comprises a single-stranded 5' or 3' section which hybridizes to the target sequence (the target binding sequence) and an intramolecularly base-paired secondary structure adjacent to the target binding sequence. The detector oligonucleotides of the invention further comprise a donor/acceptor dye pair linked to the detector oligonucleotide such that donor fluorescence is quenched when the secondary structure is intramolecularly base-paired and unfolding or linearization of the secondary structure results in a decrease in fluorescence quenching. Cleavage of an oligonucleotide refers to breaking the phosphodiester bonds of both strands of a DNA duplex or breaking the phosphodiester bond of single-stranded DNA. This is in contrast to nicking, which refers to breaking the phosphodiester bond of only one of the two strands in a DNA duplex.

The detector oligonucleotides of the invention for homogeneous real time fluorescent tSDA comprise a sequence which forms an intramolecularly base-paired secondary structure under the selected reaction conditions for primer extension or hybridization. The secondary structure is positioned adjacent to the target binding sequence of the detector oligonucleotide so that at least a portion of the target binding sequence forms a single-stranded 3' or 5' tail. As used herein, the term "adjacent to the target binding sequence" means that all or part of the target binding sequence is left single-stranded in a 5' or 3' tail which is available for hybridization to the target. That is, the secondary structure does not comprise the entire target binding sequence. A portion of the target binding sequence may be involved in the intramolecular base-pairing in the secondary structure, it may include all or part of a first sequence involved in intramolecular base-pairing in the secondary structure, it may include all or part of a first sequence involved in intramolecular base-pairing in the secondary structure but preferably does not extend into its complementary sequence. For example, if the secondary structure is a stem-loop structure (e.g., a "hairpin") and the target binding sequence of the detector oligonucleotide is present as a single-stranded 3' tail, the target binding sequence may also extend through all or part of the first arm of the stem and, optionally, through all or part of the loop. However, the target binding sequence preferably does not extend into the second arm of the sequence involved in stem intramolecular base-pairing. That is, it is desirable to avoid having both sequences involved in intramolecular base-pairing in a secondary structure capable of hybridizing to the target. Mismatches in the intramolecularly base-paired portion of the detector oligonucleotide secondary structure may reduce the magnitude of the change in fluorescence in the presence of target but are acceptable if assay sensitivity is not a concern. Mismatches in the target binding sequence of the single-stranded tail are also acceptable but may similarly reduce assay sensitivity and/or specificity. However, it is a feature of the invention described herein that perfect base-pairing in both the secondary structure and the target binding sequence does not compromise the reaction. Perfect matches in the sequences involved in hybridization improve assay specificity without negative effects on reaction kinetics.

When added to the amplification reaction, the detector oligonucleotide signal primers of the invention are converted to double-stranded form by hybridization and extension of an amplification primer as described above. Strand displacement by the polymerase also unfolds or linearizes the secondary structure and converts it to double-stranded by synthesis of a complementary strand. The RERS, if present, also becomes double-stranded and cleavable or nickable by the restriction endonuclease. As the secondary structure is unfolded or linearized by the strand displacing activity of the polymerase, the distance between the donor and acceptor dye is increased, thereby reducing quenching of donor fluorescence. The associated change in fluorescence of either the donor or acceptor dye may be monitored or detected as an indication of amplification of the target sequence. Cleavage or nicking of the RERS generally further increases the magnitude of the change in fluorescence by producing two separate fragments of the double-stranded secondary amplification product, each having one of the two dyes linked to it. These fragments are free to diffuse in the reaction solution, further increasing the distance between the dyes of the donor/acceptor pair. An increase in donor fluorescence intensity or a decrease in acceptor fluorescence intensity may be detected and/or monitored as an indication that target amplification is occurring or has occurred, but other fluorescence parameters which are affected by the proximity of the donor/acceptor dye pair may also be monitored. A change in fluorescence intensity of the donor or acceptor may also be detected as a change in a ratio of donor and/or acceptor fluorescence intensities. For example, a change in fluorescence intensity may be detected as a) an increase in the ratio of donor fluorophore fluorescence after linearizing or unfolding the secondary structure and donor fluorophore fluorescence in the detector oligonucleotide prior to linearizing or unfolding, or b) as a decrease in the ratio of acceptor dye fluorescence after linearizing or unfolding and acceptor dye fluorescence in the detector oligonucleotide prior to linearizing or unfolding.

The oligonucleotides as described may also be useful in other amplification assays with or without modification. One of ordinary skill in the art would be capable of adapting the oligonucleotide sequences or portions of the oligonucleotide sequences as described herein for other amplification assays. For example, the oligonucleotide described herein may be useful in PCR, TMA, and LCR with or without modification.

It will be apparent that, in addition to SDA, the detector oligonucleotides of the invention may be adapted for use as signal primers in other primer extension amplification methods (e.g., PCR, 3SR, TMA or NASBA). For example, the methods may be adapted for use in PCR by using PCR amplification primers and a strand displacing DNA polymerase which lacks 5'-3' exonuclease activity (e.g., Sequencing Grade Taq from Promega or exo.sup.—Vent or exo.sup.—Deep Vent from New England BioLabs) in the PCR. The detector oligonucleotide signal primers hybridize to the target downstream from the PCR amplification primers, are displaced and are rendered double-stranded essentially as described for SDA. In PCR any RERS may optionally be selected for use in the detector oligonucleotide, as there are typically no modified deoxynucleoside triphosphates present which might induce nicking rather than cleavage of the RERS. As thermocycling is a feature of amplification by PCR, the restriction endonuclease is preferably added at low temperature after the final cycle of primer annealing and extension for end-point detection of amplification. However, a thermophilic restriction endonuclease which remains active through the high temperature phases of the PCR reaction could be present during amplification to provide a real-time assay. As in SDA systems, linearization of the secondary structure and separation of the dye pair reduces fluorescence quenching, with a change in a fluorescence parameter such as intensity serving as an indication of target amplification.

The change in fluorescence resulting from unfolding or linearizing of the detector oligonucleotides may be detected at a selected endpoint in the reaction. However, because linearized secondary structures are produced concurrently with hybridization or primer extension, the change in fluorescence may also be monitored as the reaction is occurring, i.e., in "real-time". This homogeneous, real-time assay format may be used to provide semi quantitative or quantitative information about the initial amount of target present. For example, the rate at which fluorescence intensity changes during the unfolding or linearizing reaction (either as part of target amplification or in non-amplification detection methods) is an indication of initial target levels. As a result, when more initial copies of the target sequence are present, donor fluorescence more rapidly reaches a selected threshold value (i.e., shorter time to positivity). The decrease in acceptor fluorescence similarly exhibits a shorter time to positivity, detected as the time required for reaching a selected minimum value. In addition, the rate of change in fluorescence parameters during the course of the reaction is more rapid in samples containing higher initial amounts of target than in samples containing lower initial amounts of target (i.e., increased slope of the fluorescence curve). These or other measurements as is known in the art may be made as an indication of the presence of target or as an indication of target amplification. The initial amount of target is typically determined by comparison of the experimental results to results for known amounts of target.

Assays for the presence of a selected target sequence according to the methods of the invention may be performed in solution or on a solid phase. Real-time or endpoint homogeneous assays in which the detector oligonucleotide functions as a primer are typically performed in solution. Hybridization assays using the detector oligonucleotides of the invention may also be performed in solution (e.g., as homogeneous real-time assays) but are also particularly well-suited to solid phase assays for real-time or endpoint detection of target. In a solid phase assay, detector oligonucleotides may be immobilized on the solid phase (e.g., beads, membranes or the reaction vessel) via internal or terminal labels using methods known in the art. For example, a biotin-labeled detector oligonucleotide may be immobilized on an avidin-modified solid phase where it will produce a change in fluorescence when exposed to the target under appropriate hybridization conditions. Capture of the target in this manner facilitates separation of the target from the sample and allows removal of substances in the sample which may interfere with detection of the signal or other aspects of the assay.

For commercial convenience, oligonucleotides useful for specific detection and identification of *T. vaginalis* AP65-1 nucleic acids may be packaged in the form of a kit. Typically, such a kit contains at least one oligonucleotide described herein. Reagents for performing a nucleic acid amplification reaction may also be included with the *T. vaginalis* AP65-1-specific oligonucleotides. For example, buffers, other oligonucleotides, nucleotide triphosphates, enzymes, etc. may be included. The components of the kit may be packaged together in a common container. Optionally instructions may be included that illustrate one described embodiment for performing a specific embodiment of the inventive methods. Other optional components may also be included in the kit, e.g., an oligonucleotide tagged with a label suitable for use as an assay probe, and/or reagents or means for detecting the label.

In one embodiment a kit may include at least one oligonucleotide useful in the context of SDA. Oligonucleotides described herein may be useful as amplification primers, bumper primers, or probes.

In another embodiment, the kit may include at least one oligonucleotide described herein and optional components useful in the context of SDA. Such optional components may be buffers, nucleotide triphosphates, enzymes, etc. Optionally, reagents for simultaneously detecting a target sequence, such as a probe, may be included in the kit. One skilled in the art would understand how to optimize such a kit for amplification reactions to detect and identify *T. vaginalis* utilizing the oligonucleotides described herein.

In yet another embodiment, the kit may be used to detect and diagnose whether a clinical sample contains *T. vaginalis* AP65-1 DNA. The clinical sample may be added to the kit so that a nucleic acid sequence may be amplified and detected using the oligonucleotides described herein.

Furthermore, the kit may include oligonucleotides and reagents for SDA in dried or liquid format. The components of the kit may be more stable and easily manipulated when in dried format. The dried components of the kit may be added or pre-treated to a solid phase such as microtiter plate, microarray, or other appropriate receptacle, where the sample and SDA buffer need only be added. This format facilitates assaying multiple samples simultaneously and is useful in high-throughput methods. The BD ProbeTec™ and Viper™ XTR instruments may be used.

The following Examples illustrate specific embodiments of the invention described herein. As would be apparent to skilled artisans, various changes and modifications are possible, and are contemplated within the scope of the invention described.

EXAMPLES

Example 1—Assay Sensitivity

The analytical sensitivity of *Trichomonas vaginalis* ATCC 30001 was evaluated using the SDA assay at $10^4$/rxn, $10^3$/rxn and $10^2$/rxn containing a Bicine/KOH buffer (pH 8.6) with co-solvents. The SDA system that targets the conserved region of the AP56-1 gene was tested against four replicates of the AP56-1 gene (Table 4). The sensitivity for the *T. vaginalis* SDA assay can be assumed to be equal to or less than 20 target copies per assay.

TABLE 4

Assay Sensitivity

| Replicate | $10^4$/rxn | $10^3$/rxn | $10^2$/rxn |
|---|---|---|---|
| 1 | Positive | Positive | Positive |
| 2 | Positive | Positive | Positive |
| 3 | Positive | Positive | Positive |
| 4 | Positive | Positive | Positive |

The AP65-1 gene SDA assay targets a 75 bp region of the AP65-1 gene between base pairs 402-477.

Example 2: Taqman® PCR System for Detecting AP65-1

Sets of Probes were designed to perform Taqman® PCR on the AP65-1 gene. Taqman® real-time PCR is a type of quantitative PCR. Taqman® uses a fluorogenic probe which is a single stranded oligonucleotide of 20-26 nucleotides and is designed to bind only the DNA sequence between the two PCR primers. In Taqman®, reporter dyes and quencher dyes are attached to the probe. The probe is annealed to the DNA by alternating the temperature to denature and re-anneal the DNA. The Taq polymerase adds nucleotides to the target DNA and this removes the Taqman® probe from the template DNA. When the reporter dye is separated from the quencher dye, the reporter dye emits energy which is detectable. The energy is quantified by a computer, which provides a signal indicating that the target was detected.

To practice Taqman® PCR, two PCR primers with a preferred product size of 50-150 base pairs and a probe with a fluorescent reporter or fluorophore (e.g. 6-carboxyfluorescein (FAM) and tetrachlorofluorescin (TET)) and a quencher such as tetramethylrhodamine (TAMRA) covalently attached to its 5' and 3' ends are used. Suitable fluorescent reporters and fluorophores are well known and not described in detail herein. Three exemplary Taqman® probe sets for use in the highly conserved AP65-1 gene are described in Table 7 below. Each probe set consists of a forward primer (FP), a reverse primer (RP) and a probe (P).

TABLE 7

Examples of Taqman PCR Probes Sets

| SEQ ID NO: | Name | Description | 5' Sequence 3' | ~Tm (° C.) | ORF Location (bp) |
|---|---|---|---|---|---|
| SEQ ID NO: 12 | AP65-1 Taqman® FP | AP65-1 Taqman® Forward Primer | GAAGATTCTGGCAAGATCAAGGA | 58 | 448-470 |
| SEQ ID NO: 13 | AP65-1 Taqman® RP | AP65-1 Taqman® Reverse Primer | ACGACAATGCAGCGGATGT | 59 | 497-515 |
| SEQ ID NO: 14 | AP65-1 Taqman® P | AP65-1 gene Taqman® Probe | ATCCTCCGCAACTACCCACGCCA | 69 | 472-494 |
| SEQ ID NO: 15 | AP65-1 Taqman® FP2 | AP65-1 gene Taqman® Forward Primer 2 | TTACACACCAACTGTCGGTGAAG | 59 | 369-391 |
| SEQ ID NO: 16 | AP65-1 Taqman® RP2 | AP65-1 gene Taqman® Reverse Primer 2 | ATGTAGATGCCGCGGTATGAT | 58 | 420-440 |
| SEQ ID NO: 17 | AP65-1 Taqman® P2 | AP65-1 gene Taqman® Probe 2 | TTGCCAGAAGTGGGCTACACACACCGTC | 70 | 393-418 |
| SEQ ID NO: 18 | AP65-1 Taqman® FP3 | AP65-1 gene Taqman® Forward Primer 3 | CAGAGGAAACAATGCCAATTCTT | 58 | 347-369 |

TABLE 7-continued

Examples of Taqman PCR Probes Sets

| SEQ ID NO: | Name | Description | 5' Sequence 3' | ~Tm (° C.) | ORF Location (bp) |
|---|---|---|---|---|---|
| SEQ ID NO: 19 | AP65-1 Taqman® RP3 | AP65-1 gene Taqman® Reverse Primer 3 | TGACGGTGTGTAGCCCACTTC | 60 | 399-419 |
| SEQ ID NO: 20 | AP65-1 Taqman® P3 | AP65-1 gene Taqman® Probe 3 | ACACCAACTGTCGGTGAAGCTTGCC | 68 | 373-397 |

The probes are designed to anneal to the ORF location in the AP65-1 gene that is noted in the Table. FIG. 2 illustrates the binding sites on the AP65-1 gene for the primers and probes described in Table 7.

In addition to the primers and probes, Taqman® PCR requires reagents that are used for regular PCR (e.g. polymerase, free nucleotides) as well as a real-time PCR machine for analyzing the data. The reagents and equipment are well known to those skilled in the art and are not discussed in detail herein.

Although the invention herein has been described with reference to particular embodiments, it is to be understood that these embodiments are merely illustrative of the principles and applications of the invention described herein. It is therefore to be understood that numerous modifications may be made to the illustrative embodiments and that other arrangements may be devised without departing from the spirit and scope of the invention described herein as defined by the appended claims.

The invention claimed is:

1. A plurality of oligonucleotide primers and a probe for the detection of the AP65-1 gene of *Trichomonas vaginalis*, comprising a first oligonucleotide primer comprising SEQ ID NO: 15, a second oligonucleotide primer comprising SEQ ID NO: 16 and a probe comprising SEQ ID NO: 17, wherein the first and second oligonucleotide primers and the probe all are capable of hybridizing to the AP65-1 gene within the SEQ ID NO: 24 portion of the AP65-1 gene.

2. The plurality of oligonucleotide primers and the probe of claim 1, wherein the probe comprises a detectable label.

3. The plurality of oligonucleotide primers and the probe of claim 2, wherein the detectable label comprises a dye.

4. The plurality of oligonucleotide primers and the probe of claim 1, wherein the probe comprises a reporter dye and a quencher dye.

5. The plurality of oligonucleotide primers and the probe of claim 4, wherein the quencher dye is tetramethylrhodamine (TAMRA).

6. The plurality of oligonucleotide primers and the probe of claim 1, wherein the probe comprises a fluorescent reporter or a fluorophore.

7. The plurality of oligonucleotide primers and the probe of claim 6, wherein the fluorophore is 6-carboxyfluorescein (FAM) or tetrachlorofluorescin (TET).

8. The plurality of oligonucleotide primers and the probe of claim 1, wherein the probe comprises a fluorophore at the 5' end and a fluorescence quencher at the 3' end.

9. A kit for the amplification detection of *Trichomonas vaginalis*, comprising: a plurality of primers and a probe,
wherein the plurality of primers comprises a first oligonucleotide primer comprising SEQ ID NO: 15 and a second oligonucleotide primer comprising SEQ ID NO: 16 both capable of hybridizing to the AP65-1 gene of *Trichomonas vaginalis* within the SEQ ID NO: 24 portion of the AP65-1 gene; and
wherein the probe comprises SEQ ID NO: 17.

10. The kit of claim 9, wherein the probe comprises a detectable label.

11. The kit of claim 9, wherein the probe comprises a reporter dye and a quencher dye.

12. The kit of claim 11, wherein the quencher dye is tetramethylrhodamine (TAMRA).

13. The kit of claim 9, wherein the probe comprises a fluorescent reporter or a fluorophore.

14. The kit of claim 13, wherein the fluorophore is 6-carboxyfluorescein (FAM) or tetrachlorofluorescin (TET).

15. The kit of claim 9, wherein the probe comprises a fluorophore at the 5' end and a fluorescence quencher at the 3' end.

16. The kit of claim 9, comprising a DNA polymerase and/or nucleotide triphosphates.

17. The kit of claim 16, wherein the DNA polymerase is Taq polymerase.

18. The kit of claim 16, wherein one or more of the plurality of primers, the probe, the DNA polymerase, and the nucleotide triphosphates in a dried form.

19. The kit of claim 16, wherein one or more of the plurality of primers, the probe, the DNA polymerase, and the nucleotide triphosphates in a liquid form.

20. The kit of claim 9, comprising a buffer.

* * * * *